Figure 1:
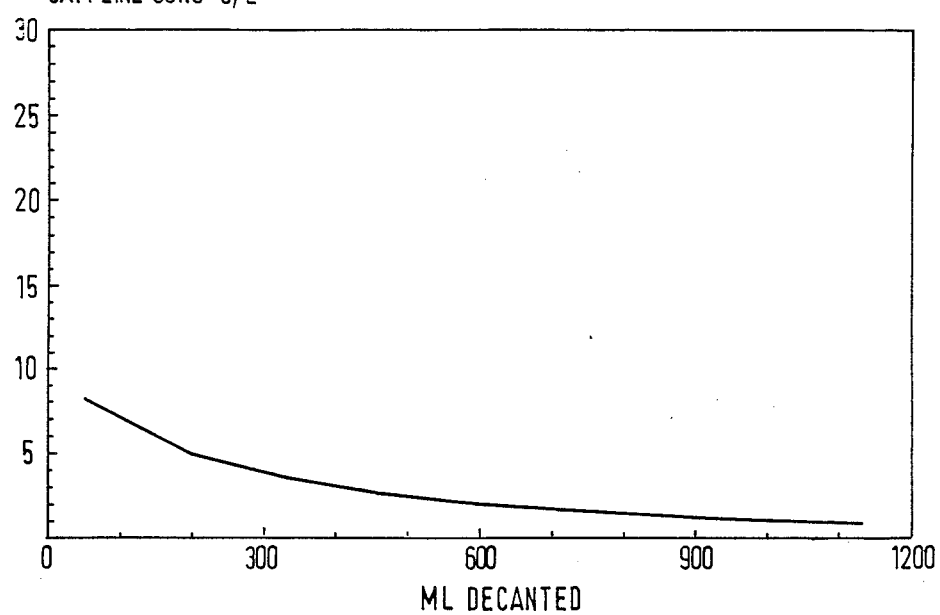

United States Patent [19]

Kaper et al.

[11] Patent Number: 4,877,631
[45] Date of Patent: Oct. 31, 1989

[54] PROCESS FOR RECOVERING CAFFEINE ABSORBED IN ACTIVATED CARBON, AND A PROCESS FOR DECAFFEINATING COFFEE

[75] Inventors: Louris Kaper, Barneveld; Roelof Klamer; Pieter J. Noomer, both of Utrecht, all of Netherlands

[73] Assignee: Douwe Egberts Koninklijke Tabaksfabriek-Koffiebranderijen-Theehandel N.V., Utrecht, Netherlands

[21] Appl. No.: 55,850

[22] Filed: Jun. 1, 1987

[30] Foreign Application Priority Data

May 30, 1986 [NL] Netherlands ............... 8601400
May 30, 1986 [NL] Netherlands ............... 8601401
Jul. 8, 1986 [NL] Netherlands ............... 8601783

[51] Int. Cl.$^4$ .................... A23F 5/22; C07D 473/12
[52] U.S. Cl. .................................... 426/422; 426/427; 426/428; 544/274; 544/275
[58] Field of Search ............ 544/274, 275; 426/422, 426/427, 428

[56] References Cited

U.S. PATENT DOCUMENTS 4,298,736 11/1981 Katz et al. ............... 544/274
4,443,601 4/1984 Karmiol et al. ............ 544/274
4,540,784 9/1985 Vitzthum et al. ........... 544/274
4,548,827 10/1985 Katz et al. ............... 426/427

FOREIGN PATENT DOCUMENTS 0111375 6/1984 European Pat. Off. ......... 426/427
0251364 1/1988 European Pat. Off. ......... 544/274

OTHER PUBLICATIONS

Umeyama, et al., Chem. Pharm. Bull., vol. 19(2), pp. 412–417, (1971).

*Primary Examiner*—Mukund J. Shah
*Assistant Examiner*—Diana G. Rivers
*Attorney, Agent, or Firm*—Cushman, Darby & Cushman

[57] ABSTRACT

A process for recovering from caffeine-loaded activated carbon by treatment of the loaded carbon with an acid. According to the present invention, activated carbon is treated with a compound having the formula

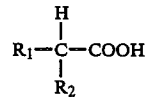

wherein $R_1$ is methyl, H or Cl, and $R_2$ is Cl, OH or phenyl.

16 Claims, 2 Drawing Sheets

PROCESS FOR RECOVERING CAFFEINE ABSORBED IN ACTIVATED CARBON, AND A PROCESS FOR DECAFFEINATING COFFEE

This invention relates to a process for recovering caffeine from loaded activated carbon by treatment with an acid.

In the literature much has been published on the recovery of caffeine from caffeine-loaded activated carbon using solutions of acids. East German patent 78568 relates to the recovery of caffeine from caffeine-loaded activated carbon using more concentrated acid than hitherto usual, giving rise to a clearly better extraction when the weakly acid solutions hitherto used. European patent application 42295 relates to the use of glacial acetic acid as a means for removing caffeine from activated carbon.

European patent application 76620 of the same applicants indicates that glacial acetic acid has the best effect indeed, but that for security reasons it is preferred to sacrifice a part of the efficiency and to use less concentrated acetic acid solutions.

Finally, European patent application 129609 relates to the use of formic acid or mixtures of formic acid with a slight amount of water for recovering caffeine. According to this last publication the use of formic acid leads to considerably better extraction results than the use of acetic acid. Formic acid, however, has a number of drawbacks, in particular the high volatility.

The object of the present invention is to provide a process for recovering caffeine from caffeine-loaded activated carbon, which process gives a clearly better extraction efficiency than the hitherto known, above described means, while the rate of desorption is higher. Other advantages of the invention will appear from the detailed discussion of the various preferred forms.

According to the invention the process for recovering caffeine from caffeine-loaded activated carbon is characterized by treating the activated carbon with an acid having the formula

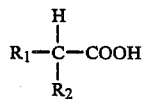

wherein $R_1$ is methyl, H or Cl is methyl, H or Cl and $R_2$ is an electron-attracting group.

Surprisingly, it has turned out that these acids alone, or in combination with each other or with other acids give excellent results in the removal of caffeine from caffeine-loaded activated carbon. Preferably, this treatment takes place in a continuous countercurrent extraction.

According to a first preferred form the caffeine-loaded activated carbon is treated with mono- and/or dichloroacetic acid.

In another preferred form the invention is characterized by treating the activated carbon with an acid having the above formula, wherein $R_1$ is methyl or H and $R_2$ is OH.

Mono- and/or dichloroacetic acid, lactic acid but also glycolic acid have proved to be particularly suitable means for recovering caffeine from activated carbon, which means give no problems with respect to roastability or volatility. Besides, it has turned out that these are excellent extracting agents leading to very high extraction efficiencies while the initial extraction is also very high, which is of special importance in continuous countercurrent methods. By a very high initial extraction is meant that upon contact of caffeine-free acid with loaded activated carbon a relatively large part of the caffeine present is nearly immediately released from the activated carbon. It will be clear that this is advantageous to a continuous countercurrent extraction because this means that the activated carbon substantially released from caffeine is subjected to a very efficient final extraction.

Moreover, a number of these acids also originally occur in coffee. This means that it is not necessary to thermally regenerate the treated carbon before reusing them.

It is observed that lactic acid occurs in two isomeric forms. Whether D-lactic acid, L-lactic acid or a mixture thereof is used has no effect on the present invention. So for economical reasons a racemic mixture is preferably used.

According to a specific preferred form the acids used according to the invention may be combined with other acids, such as formic acid, acetic acid and/of propionic acid.

The process according to the invention is preferably carried out at a temperature of more than 100° C. because an efficient extraction takes place at these temperatures. It is not necessary, however, to use superatmospheric pressures, which is of course a clear advantage. The upper limit of the temperature is not critical but should not be higher than the temperatures at which the various components become too volatile or disintegrate. Preferably, the upper limit does not exceed 200° C. and is more particularly at 150° C. because no additional advantages are to be obtained above the last mentioned temperature.

According to another preferred form of the invention liquid benzoic acid is used for recovering caffeine from activated carbon. In view of the high melting point of benzoic acid, 122° C. This agent gives hardly, if any, problemms with respect to flammability or volatility, as is the case with acetic acid. Moreover, it has turned out that liquid benzoic acid is an excellent extracting agent which permits to obtain very high extraction efficiencies, while the initial extraction is also very high, which is of special importance in continuous countercurrent methods.

It is a further advantage of benzoic acid that it is generally recognized as a safe product in food applications so that extracted carbon in which a slight amount of benzoic acid may still be present can be reused for decaffeinating coffee without causing problems.

The process according to this preferred form should of course be carried out at temperatures at which benzoic acid is liquid. In view of the melting point of benzoic acid of 122° C., temperatures ranging from 130° to 160° C. are preferred although higher or lower temperatures are also applicable, but lower temperatures are not preferred because this involves the risk that benzoic acid will solidify in case of insufficient heating, which results in the apparatus becoming clogged. Temperatures above 160° C. generally offer no advantages over temperatures below 160° C., while there is also a risk that certain products will disintegrate.

In connection with the relatively low volatility of benzoic acid it is not necessary to operate under super atmospheric pressures. This is of course an advantage from the viewpoint of investments and energy consumption.

According to the invention the acids described are used as such or in admixture. If required, also mixtures with formic acid, acetic acid and/or propionic acid may be used. In general, the concentration of the acids described is at least 50% by weight, more particularly they are used alone, that is to say they are not used with formic acid, acetic acid and/or propionic acid.

As indicated the treatment preferably takes place countercurrently, which leads to relatively short extraction times. The most appropriate extraction times and extraction amounts can be established by those skilled in the art by means of routine tests. The amount of extraction liquid per mount of activated carbon can be very small as a result of the highly efficient extraction, and in general, a fivefold to tenfold amount of extracting agent relative to the amount of loaded activated carbon will be sufficient. These amounts are considerably lower than the amounts required according to the state of the art, in which at least tenfold to twentyfold amounts are necessary. Of course, large amounts can also be used according to the invention, but this is not necessary. The caffeine-loaded carbon will generally originate from processes for removing caffeine from green coffee. Examples of such processes are described in European patent applications 40712, 111375 and 8398.

After the caffeine has been removed from the carbon, it can be removed from the solution in the known manner, e.g. by means of crystallization.

After removal of the solvent and/or regeneration the carbon which is nearly completely liberated from caffeine can be reused for absorption of caffeine.

The invention also relates to a process for decaffeinating coffee by means of activated carbon, followed by recovery of the caffeine from the carbon, which is characterized by treating the activated carbon using the process according to the invention.

The invention will be illustrated by some examples but is not restricted thereto.

EXAMPLE I

A commerical activated carbon having a caffeine load of 44 g/kg carbon and a total dry load of 225 g/kg carbon was placed in a column heated to 120° C., after which an amount dichloroacetic acid was pumped through the column from the top to the bottom at a superficial velocity of 0.4 mm/sec.

After cooling the dichloroacetic acid was analyzed by means of HPLC as to caffeine content. Of the amount of caffeine present the carbon, 80.8% by weight was desorbed.

In EP 42295 a value of 73% was found for the use of glacial acetic acid. It is therefore clear that a considerable improvement has been achieved by the invention.

EXAMPLE II AND COMPARATIVE EXAMPLE

In the manner described in Example I tests were carried out with dichloroacetic acid and acetic acid at 112° C. 100 g of the carbon was treated with the solvents, and a comparison was made between the caffeine contents in the first two fractions of 25 ml. The results are listed in the table.

| fraction | acetic acid caffeine conc. (g/l) | dichloro acetic acid caffeine conc. (g/l) |
|---|---|---|
| 1 | 16.3 | 26.6 |
| 2 | 13.8 | 17.5 |

These data clearly show that a superior initial extraction is obtained by the invention.

COMPARATIVE EXAMPLE

Desorption by means of acetic acid

In a 500 ml round-bottomed flask provided with reflux cooling, 100 g commercial carbon (81.7 g carbon) preloaded with caffeine and other components was desorbed by means of acetic acid. The desorption took place by repeatedly decanting the acetic acid, after which clean acetic acid was added again. The reflux time per charge was 30–40 minutes at 118° C. The results are listed in table A.

EXAMPLE III

Desorption by means of benzoic acid.

In a 500 ml round-bottomed flask provided with a stirrer, 100 g commercial (81.7 g carbon) carbon preloaded with caffeine and other components was desorbed by means of benzoic acid. The desorption took place by repeatedly decanting the benzoic acid melt, after which clean benzoic acid, in molten form, was added again. The stirring time per charge was 30–40 min. at 150° C. After cooling the fractions were analyzed for caffeine. The solubility of benzoic acid in water is only 2.9 g/kg. Then the amount of caffeine in the benzoic acid cannot be detected anymore. For the caffeine analysis in the benzoic acid samples, 1 g sample is weighed out and dissolved in 25 ml in acetic acid. The caffeine content is determined in this solution. The results are listed in Table B.

TABLE A

| Solvent | Acetic acid |
|---|---|
| Reflux temperature | 118° C. |
| Caffeine adsorption | 44 g/kg |
| Caffeine desorption | 35.9 g/kg |
| % Desorption/load | 81.6% |

| Decanted volume (ml) | Caffeine concentr. (g/l) | Caffeine absolute (g) | Caffeine cumulative (g) | Caffeine desorbed (%) | Volume cumulative (ml) |
|---|---|---|---|---|---|
| 55 | 8.14 | 0.4477 | 0.4477 | 12.5 | 55 |
| 150 | 4.86 | 0.7290 | 1.1767 | 32.8 | 205 |
| 130 | 3.55 | 0.4615 | 1.6382 | 45.6 | 335 |
| 120 | 2.69 | 0.3228 | 1.9610 | 54.6 | 455 |
| 115 | 2.135 | 0.2455 | 2.2065 | 61.5 | 570 |
| 112 | 1.78 | 0.1994 | 2.4059 | 67.0 | 682 |
| 110 | 1.46 | 0.1606 | 2.5665 | 71.5 | 792 |
| 120 | 1.21 | 0.1452 | 2.7117 | 75.5 | 912 |
| 110 | 1.05 | 0.1155 | 2.8272 | 78.7 | 1022 |
| 110 | 0.92 | 0.1012 | 2.9284 | 81.6 | 1132 |

TABLE B

| Solvent | benzoic acid |
|---|---|
| Temperature during stirring | 140–150° C. |
| Caffeine adsorption | 44 g/kg |
| Caffeine desorption | 39.2 g/kg |
| % Desorption/Adsorption | 89.1% |

| Decanted weight (g) | Caffeine concentr. (%) | Caffeine absolute (g) | Caffeine cumulative (g) | Caffeine desorped (%) | Weight Cumulative (g) |
|---|---|---|---|---|---|

TABLE B-continued

| Solvent | benzoic acid |
|---|---|
| Temperature during stirring | 140–150° C. |
| Caffeine adsorption | 44 g/kg |
| Caffeine desorption | 39.2 g/kg |
| % Desorption/Adsorption | 89.1% |

| | | | | | |
|---|---|---|---|---|---|
| 68.5 | 1.86 | 1.274 | 1.274 | 35.5 | 68.5 |
| 130 | 0.827 | 1.075 | 2.349 | 65.4 | 198.5 |
| 115 | 0.375 | 0.431 | 2.780 | 77.4 | 313.5 |
| 84 | 0.217 | 0.182 | 2.962 | 82.5 | 397.5 |
| 152 | 0.090 | 0.137 | 3.099 | 86.3 | 549.5 |
| 89 | 0.050 | 0.045 | 3.144 | 87.6 | 638.5 |
| 84 | 0.035 | 0.029 | 3.174 | 88.4 | 722.5 |
| 75 | 0.013 | 0.010 | 3.183 | 88.7 | 797.5 |
| 107 | 0.010 | 0.011 | 3.193 | 88.9 | 904.5 |
| 165 | 0.003 | 0.005 | 3.199 | 89.1 | 1069.5 |

Figure 2:
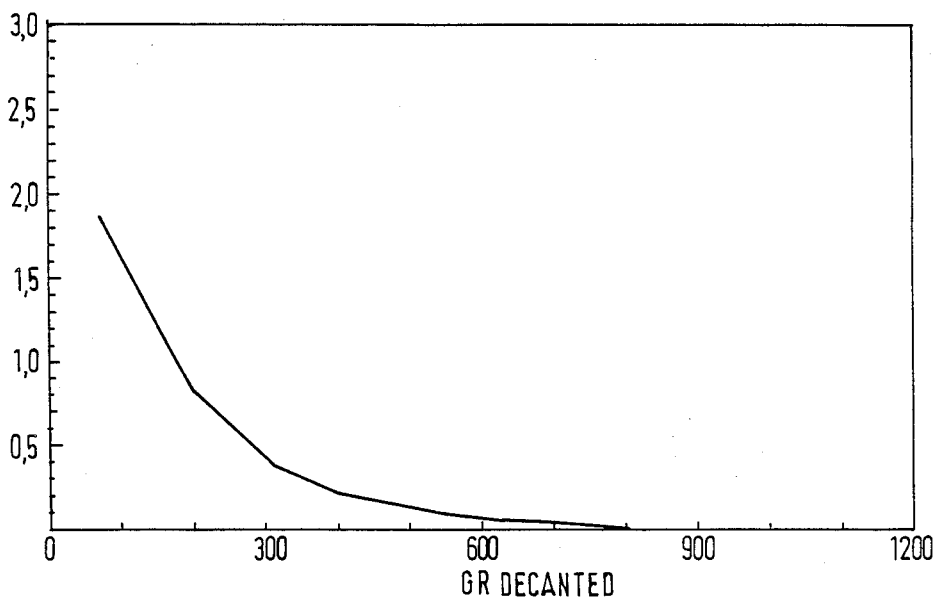
Figure 3:
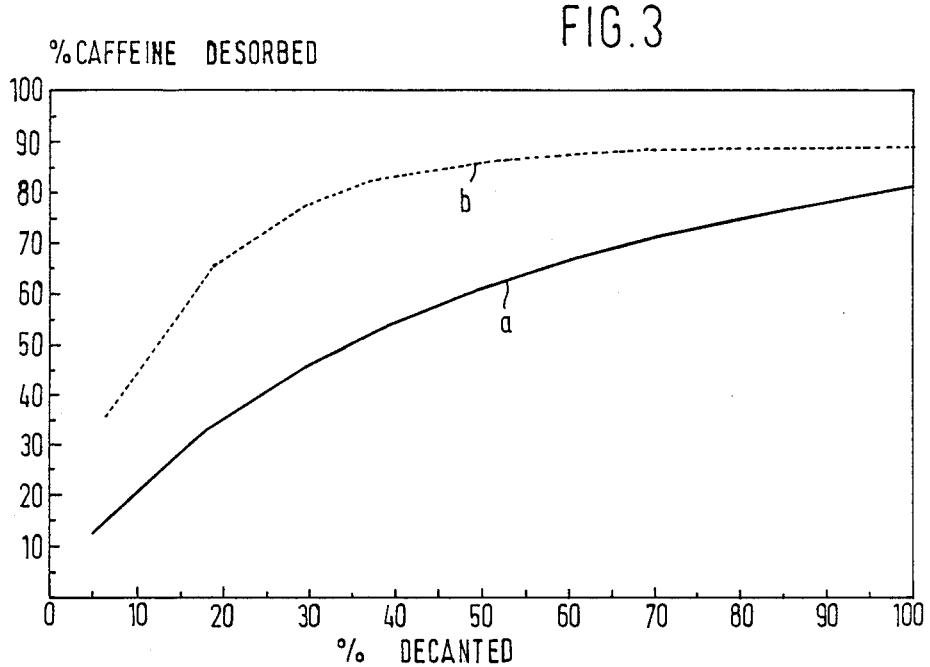

The variation of the caffeine concentration as a function of the decanted amount of acid is graphically represented by FIGS. 1 and 2. FIG. 3 graphically represents the percentage of desorbed caffeine as a function of the percentage of the decanted amount of acid in relation to the total amount of decanted acid (line a is acetic acid and line b benzoic acid).

Under the given process conditions the caffeine desorption effected with benzoic acid leads to better results than the desorption with acetic acid. For benzoic acid a desorption percentage of 89.1% was obtained. For acetic acid this was 81.6%.

EXAMPLE IV 100 g of a commercial activated carbon having a caffeine load of 44 g/kg carbon (81.6 g unloaded carbon) was desorbed with lactic acid (85–90%) in water by pumping 3 l of this solution over a carbon column having a temperature of 100°–105° C. (downflow) in about 4 hours. The eluent was collected in a number of fractions and analyzed for caffeine after cooling. The results are listed in the table.

TABLE C

| Eluent | lactic acid (85–90%) | | | |
|---|---|---|---|---|
| Elution temperature | 110° C. at the double wall of the carbon column, 100–105° C. within the column | | | |
| Caffeine desorption | 30.38 g/kg | | | |
| Desorption efficiency | 70.08% | | | |

| fraction no. | range (ml) | volume (ml) | weight (g) | caff.conc. (g/l) | caffeine (g) |
|---|---|---|---|---|---|
| 1 | 0–25 | 25.2 | 30.14 | 4.915 | 0.122 |
| 2 | 25–50 | 25.0 | 29.60 | 4.586 | 0.115 |
| 3 | 50–100 | 39.5 | 46.78 | 4.119 | 0.163 |
| 4 | 100–200 | 90 | 107.48 | 3.886 | 0.350 |
| 5 | 200–350 | 140 | 166.17 | 2.216 | 0.310 |
| 6 | 350–500 | 140 | 159.53 | 1.442 | 0.202 |
| 7 | 500–1000 | 500 | 596.57 | 0.949 | 0.474 |
| 8 | 1000–1500 | 500 | 597.11 | 0.554 | 0.277 |
| 9 | 1500–2000 | 500 | 596.12 | 0.310 | 0.155 |
| 10 | 2000–2500 | 500 | 596.24 | 0.256 | 0.128 |
| 11 | 2500–3000 | 412 | 488.56 | 0.208 | 0.085 |
| total | | 2911.8 | 3461.50 | | 2.516 |

Figure 4:
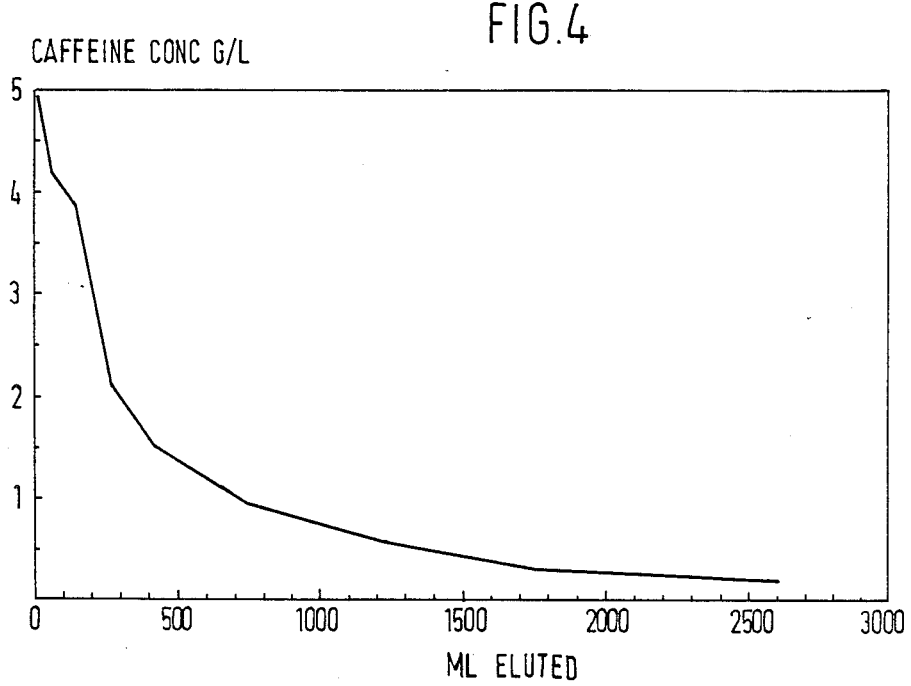

The results of this test are shown in FIG. 4.

EXAMPLE V

Green coffee was decaffeinated using the process described in European patent application 111375. The caffeine loaded activated carbon was then subjected to a countercurrent treatment with a 90% solution of lactic acid in water. Good yields were obtained.

We claim:

1. A process for recovering caffeine from caffeine-loaded activated carbon by treatment of the loaded carbon with an acid, comprising the steps of treating the activated carbon with benzoic acid or a compound having the formula

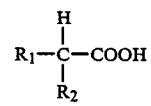

wherein $R_1$ is methyl, H or Cl, and $R_2$ is Cl, OH or phenyl.

2. A process as claimed in claim 1, wherein $R_1$ is methyl, and $R_2$ is OH.

3. A process as claimed in claim 1, wherein $R_1$ is H and $R_2$ is Cl, OH or phenyl.

4. A process as claimed in claim 1, wherein $R_1$ and $R_2$ are both Cl.

5. A process as claimed in claim 1, further including subjecting the activated carbon to a countercurrent treatment with the acid.

6. A process according to claim 3, wherein said compound is mono- and/or dichloroacetic acid.

7. A process as claimed in claim 1, further including treating the activated carbon at a temperature of more than 100° C.

8. A process as claimed in claim 1, wherein said compound is liquid benzoic acid.

9. A process as claimed in claim 8, further including treating the activated carbon at a temperature of at least 130° C.

10. A process as claimed in claim 9, further including treating the carbon at a temperature of not more than 160° C.

11. A process as claimed in claim 1, further including recovering the caffeine from the resulting solution by means of crystallization.

12. A process for decaffeinating coffee comprising the steps of absorbing the caffeine on activated carbon, and recovering the caffeine from the caffeine loaded activated carbon wherein the improvement comprises recovering the caffeine from the caffeine loaded activated carbon by treatment of the loaded carbon with an acid, including the steps of treating the activated carbon with a compound having the formula

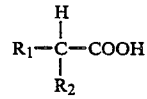

wherein $R_1$ is methyl, H or Cl, and $R_2$ is Cl, OH or phenyl.

13. A process for recovering caffeine from caffeine-loaded activated carbon by treatment of the loaded carbon with an acid, comprising the steps of treating the activated carbon with a compound having the formula

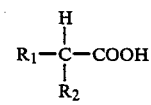

wherein $R_1$ is methyl, H or Cl, and $R_2$ is Cl, or OH.

14. A process for recovering caffeine from caffeine-loaded activated carbon by treating the loaded carbon with an acid selected from the group consisting of monochloroacetic acid, dichloroacetic acid, lactic acid, glycolic acid, benzoic acid, and mixtures thereof.

15. A process for recovering caffeine from caffeine-loaded activated carbon by treating of the loaded carbon with an acid selected from the group consisting of monochloroacetic acid, dichloroacetic acid, lactic acid, glycolic acid, benzoic acid, and mixtures thereof, said acid being in combination with formic acid, acetic acid and/or propionic acid.

16. A process for recovering caffeine from caffeine-loaded activated carbon by treating of the loaded carbon with an acid selected from the group consisting of monochloroacetic acid, dichloroacetic acid, lactic acid, glycolic acid, and mixtures thereof.

* * * * *